United States Patent [19]
Naujokas

[11] Patent Number: 5,821,381
[45] Date of Patent: Oct. 13, 1998

[54] LOW PRESSURE PROCESS FOR PURIFYING CRUDE POLYESTER BY SUBLIMATION

[75] Inventor: Andrius A. Naujokas, Webster, N.Y.

[73] Assignee: Eastman Kodak Company, Rochester, N.Y.

[21] Appl. No.: 792,049

[22] Filed: Feb. 3, 1997

[51] Int. Cl.$^6$ ..................................................... C07C 67/48
[52] U.S. Cl. ................................................................ 560/78
[58] Field of Search ................................................ 560/78

[56] References Cited

U.S. PATENT DOCUMENTS

| | | |
|---|---|---|
| 3,257,335 | 6/1966 | Whitfield, Jr. et al. ................. 260/2.3 |
| 3,907,868 | 9/1975 | Currie et al. ......................... 260/475 D |
| 4,163,860 | 8/1979 | Delattre et al. ............................. 56/96 |
| 5,414,022 | 5/1995 | Toot, Jr. et al. ........................... 521/48 |

*Primary Examiner*—Terressa Mosley
*Attorney, Agent, or Firm*—Arthur H. Rosenstein

[57] ABSTRACT

There is described a process for depolymerizing polyesters such as polyethylene terephthalate polyester to monomer components comprising esters such as dimethyl terephthalate and purifying the ester by sublimation, which purified ester can then be used to make virgin polyester.

15 Claims, 1 Drawing Sheet

LOW PRESSURE PROCESS FOR PURIFYING CRUDE POLYESTER BY SUBLIMATION

FIELD OF THE INVENTION

This invention relates to a process for purifying crude esters such as dimethyl terephthalate, dimethyl naphthalate, and the like, and specifically to recover ester and glycol components from polyesters such as scrap polyesters.

BACKGROUND OF THE INVENTION

Polyesters such as polyethylene terephthalate (PET) have outstanding physical properties for a number of uses, such as in textile, film and other applications. It has been found to be particularly useful as a film base for magnetic recording materials and as film base in the photographic industry. The polymer is a linear polyester produced from ethylene glycol and dimethyl terephthalate using conventional polymerization processes. Due to relatively high cost of the polyester and to minimize the need for disposal, it is desirable to recycle and reuse waste polyesters.

Many distinctly different routes have been used to recycle polyesters in general. The first route is direct recycle. This can be done when the polyester scrap is completely clean or can be cleaned by washing or other means. The cleaned polyester is used in place of virgin polyester at the appropriate point in the manufacturing process. Depending upon the manufacturing steps in the process, degradation of the polyester can occur during such steps as melting and extrusion due to thermal and shear effects. This results in the deterioration of the physical properties of the polyester, such as a lowering of molecular weight and producing side reaction products. Generally for high grade products, such as film base, recycle polyester is blended in limited amounts with virgin polyester. If the polyester scrap is contaminated, or is not thoroughly cleaned, additional degradation of properties can occur.

The second route is depolymerization of the polyester to component monomers, recovering the monomers and then using them to produce new polyester. This route has been used for recovery of monomers from polyethylene terephthalate polyester. Recovery techniques are described, for example in U.S. Pat. Nos. 5,414,022; 4,163,860; 3,907,868; and 3,257,335.

Polyesters are condensation polymers and, therefore, can be depolymerized back to the starting monomers by adding monohydric or dihydric alcohols at an excess concentration under appropriate conditions of temperature and in the presence of catalysts. If methanol is used in the process the depolymerization products are dimethyl terephthalate (DMT) and ethylene glycol (EG). In actual practice the scrap polyester contains contaminants which may be carried into the product stream. The reactions are carried out at temperatures between 200° and 280° C. and additional degradation materials may be generated during the depolymerization step that may contaminate the reaction products. Generally the crude DMT must be purified and refined to obtain polymer grade monomer. The purification typically consists of a crystallization step, washing and vacuum distillation. In the distillation step generally the product DMT is the overhead product while most of the impurities wind up in the still bottoms.

The crystallization and washing step separates the non DMT components to a certain extent only. Any impurities trapped by the DMT crystals are not washed out. The efficiency of washing also depends on the crystal size and size distribution. For instance, poorly formed crystal mats have low liquid permeability and, therefore, are difficult to wash. To prevent addition of new components to the system the washing medium is methanol. DMT has appreciable solubility in methanol. For instance, at room temperature the equilibrium solubility of DMT is about 1% by weight. Therefore, for each pound of methanol used to wash the crude DMT crystals 0.01 lb. is lost with the methanol. This reduces the process yield. The lost material must be recycled or is discarded.

The distillation step requires elevated temperatures and relatively low pressure (vacuum). Separation is accomplished by fractionation that depends on relative component volatility. For contaminants of similar volatility to DMT large number of stages are required. In some cases azeotropes may be present that will prevent separation by standard distillation. If on the other hand, both high and low volatility contaminants are present more than one distillation column may be required. Therefore, high purity feed to the DMT still is necessary to obtain polymer grade product. This necessitates purification of the crude DMT to a high degree before the final distillation step.

SUMMARY OF THE INVENTION

An object of this invention is to obtain a method for refining esters such as dimethyl terephthalate, dimethyl naphthalate (NDC) and the like, at low temperatures so as to minimize thermal degradation.

It is a further object of this invention to refine esters at process conditions which can be adjusted to separate contaminants of different properties.

It is a still further object of this invention to increase the crystal quality and size of purified esters.

It is a further object of this invention to refine esters to a solid product that can be readily packaged for storage and shipment.

The present invention involves a purification method for esters such as DMT or NDC whereby the process of sublimation is used to separate the DMT or NDC from the contaminants. The process utilizes the physical property of DMT or NDC and similar organic solids that allows vaporization and condensation without going through a liquid phase.

The crude DMT or NDC is vaporized either from a liquid or a solid phase at appropriate temperature and pressure. The vapor is then cooled by addition of a cool, inert gas and removal of sensible heat by other means such as heat exchangers whereby DMT or NDC forms crystals in the gas stream. The DMT or NDC crystals then can be settled from the gas by gravity or separated in a cyclone and removed for further processing. This process can be used with crude DMT or NDC from any PET or PEN scrap recovery process.

Figure 1:
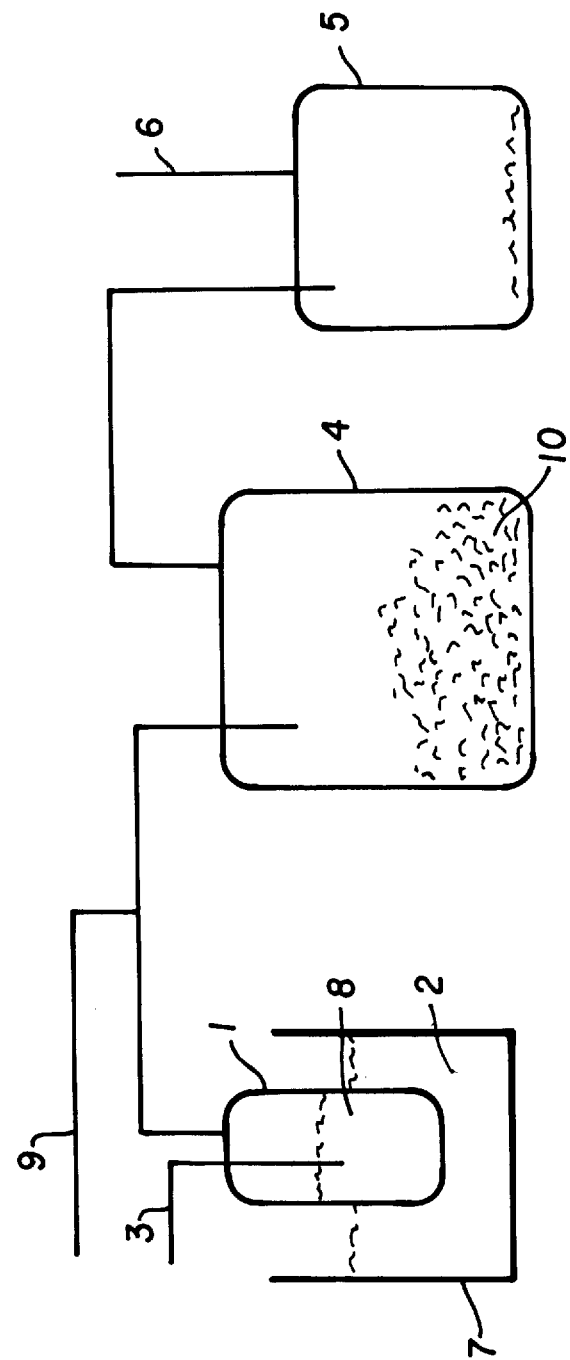
FIG. 1 is a schematic of the DMT purification process.

For a better understanding of the present invention, together with other and further objects, advantages and capabilities thereof, reference is made to the following detailed description and appended claims in connection with the preceding drawings and description of some aspects of the invention.

DETAILED DESCRIPTION OF THE PREFERRED EMBODIMENTS

The embodiment of the present invention is presented for purification of the polyethylene terephthalate diester monomer—dimethyl terephthalate. This process can also be employed for the purification of the polyethylene naphthalate and other similar diester monomers that tend to sublime. In the case of dimethyl naphthalate the purification and refining is more difficult due to high melting point and low volatility of that diester. Appropriate process conditions must be used with this material in order to obtain the required purification.

The crude polyester which may be PET or polyethylene naphthalate or other polyester are recommend and depolymerized by a variety of methanols.

The process of purifying the crude esters such as DMT involves sublimation.

Dimethyl terephthalate can be vaporized from a solid phase as well as liquid phase. Likewise the vapor phase can be condensed to a liquid as well as directly to the solid phase. The path depends of the process conditions. The DMT contaminants that may consist of residual methanol, ethylene glycol, degradation products, extraneous materials that were introduced with the polyester scrap generally have normal physical properties. That is, they have conventional vapor-liquid equilibria. Therefore, under sublimation conditions the separation of the contaminants may be accomplished under relatively mild conditions. It was found that DMT can be separated from the contaminants by adjusting temperatures and concentrations of the process. The low volatility components remain in the processing unit while the volatile contaminants are carried out with the DMT vapor. By adjusting the stream temperature and amount of dilution the volatile components can be kept above their dew points while DMT crystals are formed in the carrier gas. The volatile contaminants then can be swept out by the carrier gas out of the crystallizer vessel.

The embodiment is illustrated by way of examples

The crude DMT is refined using apparatus presented schematically in FIG. 1. The setup consists of a flask 1 containing the crude DMT 8 which is heated by immersion to the appropriate level in a molten salt bath 2 in a container 7 maintained at 250° to 300° C. Nitrogen 3 is introduced into the flask to carry the DMT vapor to the receiver. An additional stream of nitrogen 9 is added to the process stream before it enters the first receiver. This nitrogen stream is used to further control the stream composition and temperature. This allows the DMT vapor to form solid crystals. The relatively large first receiver volume reduces the gas velocity where the DMT crystals 10 are able to settle out of the gas stream. The second receiver 5 is used to capture the remaining DMT solids. The gas stream is then vented by vent 6.

The conditions under which this sublimation process takes place are as follows:

The sublimator temperature is from 140° C. to 280° C., the pressure is from vacuum to atmospheric and the carrier gas comprises from inert and non reactive carrier gas such as nitrogen or $CO_2$ or similar gases.

The embodiment of the invention is illustrated in the examples.

EXAMPLE 1

Preparation of crude DMT

DMT was produced using a laboratory scale atmospheric methanolysis process according to U.S. Pat. No. 5,051,528 using scrap film base containing various coatings and other additives. The reactor product consisted of a slurry of DMT crystals in methanol and ethylene glycol. The DMT was separated from the liquid phase by filtration and then was dried by evaporation. The crystal mat was not washed. The appearance of the solids was crystalline with a light straw color. The purity of the DMT was determined by a two hour heat stress test at 180° C. The results indicated molten DMT color of >2000 arbitrary color units. This DMT purity is not suitable to product acceptable quality polyester (PET).

The crude DMT was then purified in the apparatus shown in FIG. 1. The experimental conditions were as follows:

Temperature—205° C.

Pressure—ambient

Nitrogen flow into the flask—3 cfh

Secondary nitrogen flow—3 cfh

DMT sublimation rate—0.2 g/min

DMT/Nitrogen ratio—0.05:1

The resultant product was crystalline with crystal sizes up to ¼ inch in length. The heat stress color was about 150 arbitrary units.

EXAMPLE 2

Crude DMT was obtained from polyester recovery operations. The samples were obtained after the crystal filtration and washing step. The DMT crystals were dried by evaporation at mild conditions. The original heat stress color was about 200 arbitrary color units. Same apparatus as described above was used in the separation except only a single nitrogen injection into the DMT melt was used.

Process conditions:

Temperature—200° C.

Pressure—ambient

Nitrogen flow rate—3 cfh

DMT sublimation rate—0.3 g/min

DMT/Nitrogen ratio (by weight) 0.17:1

The resulting product consisted of needle-like crystals up to ½ inch in length. The heat stress color was about 20 arbitrary color units.

In the above examples both good and poor quality crude DMT were improved by sublimation. Washing before the sublimation step improves the DMT purity of the process.

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

I claim:

1. A process for purifying esters selected from the group consisting of dimethyl terephthalate and dimethyl naphthalate comprising:
    a) vaporizing crude esters at a temperature of from 140° to 280° C. and a pressure of from vacuum to atmospheric;
    b) crystallizing dimethyl terephthalate by adding to vaporized dimethyl terephthalate an inert gas and removing sensible heat; and
    c) settling the resulting monomeric ester crystals.

2. The process of claim 1 wherein the temperature is 205° C.

3. The process of claim 1 wherein the pressure is atmospheric.

4. The process of claim 1 wherein the inert gas is nitrogen.

5. The process of claim 1 wherein the sensible heat is removed by a heat exchanger.

6. The process of claim 1 wherein step c) is separating the ester in a cyclone.

7. The process of claim 1 wherein the ester in step a) is in a solid phase.

8. The process of claim 1 wherein the ester of step a) is in a liquid phase.

9. A process for forming pure polyester selected from the group consisting of polyethylene terephthalate and polyethylene naphthalate comprising:

a) depolymerizing crude polyester selected from the group consisting of dimethyl terephthalate and dimethyl naphthalate into its constituent monomers including an ester monomer;

b) evaporating said ester at a temperature of from 140° to 280° C. and a pressure of vacuum to atmospheric;

c) crystallizing the resulting ester in an inert gas and removing sensible heat;

d) settling the resulting ester crystals; and e) reacting the resulting purified ester with a glycol to form a polyester.

10. The process of claim 9 wherein the process is carried out at ambient pressure.

11. The process of claim 9 wherein the inert gas is nitrogen.

12. The process of claim 9 wherein the sensible heat is removed by a heat exchanger.

13. The process of claim 9 wherein step c) is separating ester in a cyclone.

14. The process of claim 9 wherein the ester in step a) is in a solid phase.

15. The process of claim 9 wherein the ester of step a) is in a liquid phase.

* * * * *